United States Patent [19]

Moore et al.

[11] E Re. 31,290

[45] Reissued Jun. 28, 1983

[54] COLOR ENDOSCOPE

[75] Inventors: William C. Moore, Skaneateles; Richard W. Newman, Auburn; Dominick Danna, Syracuse, all of N.Y.

[73] Assignee: Welch Allyn, Inc., Skaneateles Falls, N.Y.

[21] Appl. No.: 282,087

[22] Filed: Jul. 10, 1981

Related U.S. Patent Documents

Reissue of:

[64] Patent No.: 4,261,344
Issued: Apr. 14, 1981
Appl. No.: 78,300
Filed: Sep. 24, 1979

U.S. Applications:

[62] Division of Ser. No. 951,653, Oct. 16, 1978, Pat. No. 4,253,447.

[51] Int. Cl.[3] ..... A61B 1/06

[52] U.S. Cl. ..... 128/6; 358/98

[58] Field of Search ..... 128/3-11; 350/96.26; 358/1, 11, 98, 901

[56] References Cited

U.S. PATENT DOCUMENTS 4,074,306 2/1978 Kakinuma et al. ..... 128/6 X

*Primary Examiner*—John D. Yasko
*Attorney, Agent, or Firm*—Bruns & Jenney

[57] ABSTRACT

A color endoscope having a compact viewing head that is easily inserted into a relatively small opening or cavity and an electrical section that is capable of producing a readout signal containing full color image information that is compatible with standard format television for storing, displaying or otherwise processing the color information.

7 Claims, 6 Drawing Figures

COLOR ENDOSCOPE

Matter enclosed in heavy brackets [ ] appears in the original patent but forms no part of this reissue specification; matter printed in italics indicates the additions made by reissue.

BACKGROUND OF THE INVENTION

This is a division of application Ser. No. 951,653 filed Oct. 16, 1978[.], *now U.S. Pat. No. 4,253,447.*

This invention relates to an endoscope for processing color information and providing a read-out signal that is fully compatible with any standard format television equipment.

In U.S. Pat. No. 4,074,306, there is disclosed an endoscope system for producing a full color image of the region scanned by the viewing head of the system. In this prior art device, the image information contained in the viewing region of the system is separated into the three primary colors of red, green and blue, and the images then sequentially laid down, one on top of the other, on a Braun tube to recreate the original full color image. The three primary color images are created by either mechanically filtering the illuminating light brought into the cavity using a single light source and a rotating filter disc or by breaking down a reflected light image of the viewing region using a series of dichroic mirrors.

Although the prior art device performs well, it nevertheless requires special equipment to sequentially process the three independent read-out signals. Mechanically driven filter discs also can present timing and balancing problems which, under certain conditions, can be troublesome. Because the disc mounted filters move through an arcuate path of travel, a sharp, well defined edge between images, which is essential in a high speed system, cannot be obtained. Lastly, the use of dichroic mirrors and the like in the viewing head of the system increases the size of the head and thus makes it difficult to insert into relatively small body cavities or openings thereby limiting the usefulness of the instrument.

SUMMARY OF THE INVENTION

It is therefore an object of the present invention to improve endoscopes for providing color pictures of a remote viewing region.

It is another object of the present invention to provide an endoscope system that is capable of utilizing standard format video equipment for storing, displaying or otherwise processing color image information. A still further object of the present invention is to improve the illumination system used in an endoscope for producing three primary color light images of the visual information found in the viewing region of the instrument.

Another object of the invention is to eliminate the need for special read-out equipment in a color endoscope system.

Yet another object of the present invention is to simplify the component parts used in an endoscope system for providing a full color picture of the visual information contained in the object plane of the system.

A further object of the present invention is to produce an enlarged, high resolution, picture of the scene found in the viewing plane of an endoscope using standard video equipment.

These and other objects of the present invention are attained by means of an endoscope having a compact viewing head which is easily insertable into a relatively small body opening and an external electronics section that is arranged to receive color image information from the viewing head and provide a read-out signal that is fully compatible with standard format television equipment. Three separate light images, each containing data relating to an individual primary color, are generated by electrically strobbing a series of lamps having rapid response times.

BRIEF DESCRIPTION OF THE DRAWINGS

For a better understanding of these and other objects of the present invention, reference is had to the following detailed description of the invention to be read in conjunction with the following drawings, wherein.

DESCRIPTION OF THE INVENTION

Figure 1:
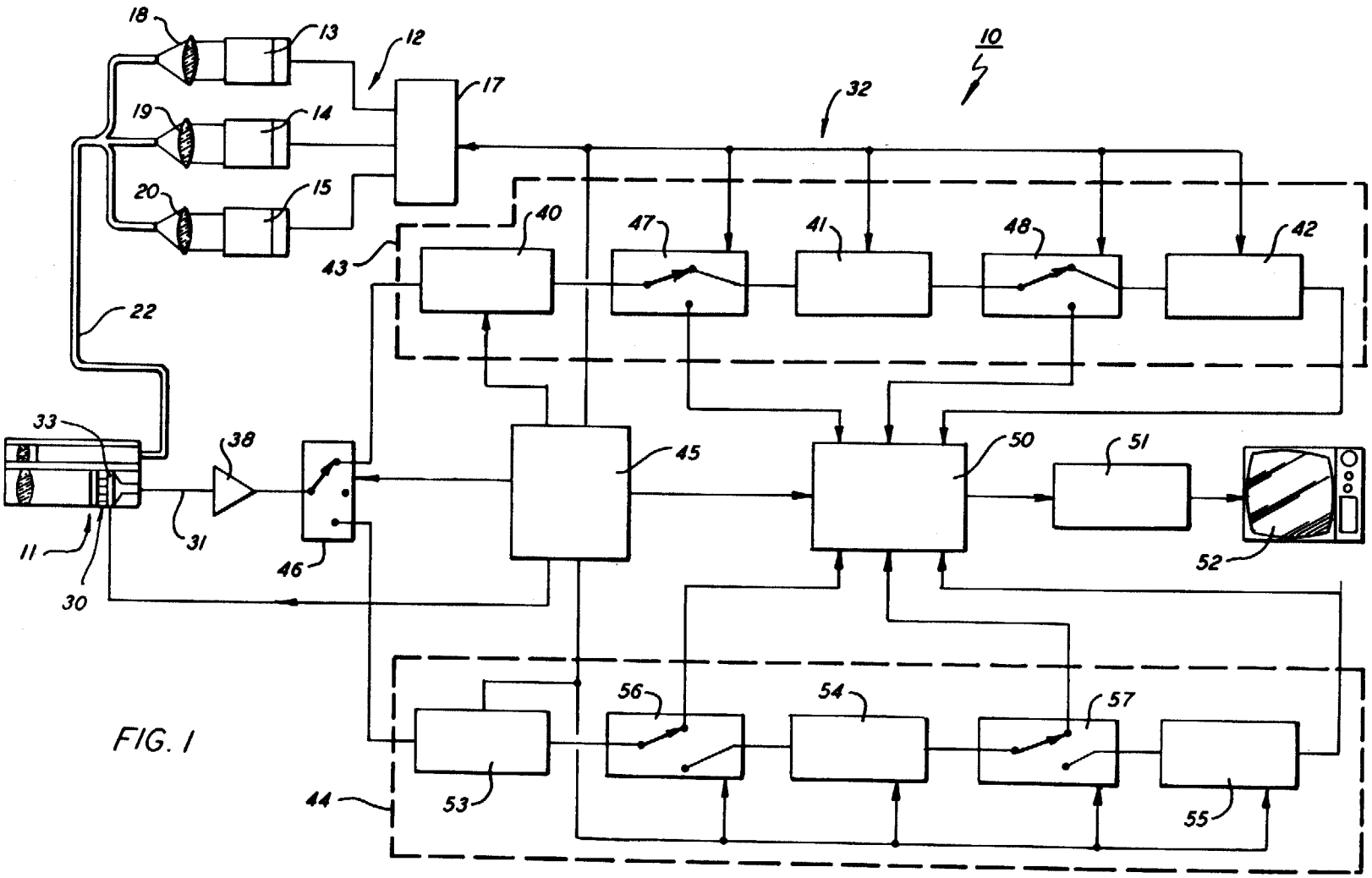
FIG. 1 is a block diagram of an endoscope system according to a first embodiment of the invention wherein a full frame interlaced picture is produced upon a standard television viewing screen.

As shown in FIG. 1 of the accompanying drawings, the endoscope of the present invention, which is generally referenced 10, is made up of a viewing head 11, which is adapted for insertion into a relatively small cavity or opening, and an electrical section 32 that is arranged to receive visual data signals from the viewing head and convert the data into an output signal that is fully compatible with standard format television equipment for storing, displaying or transmitting the signal information. This type of equipment can include but is not limited to video tape recorders, television monitors, television receivers and the like.

The present system also includes a light handling section 12 containing three individual strobe lamps 13–15 that are sequenced in a programmed firing order by means of a strobe drive 17. Positioned at the light emitting surface of the lamps are optical elements 18–20 which serve to filter the emitted light and to focus the light upon the light entrance face of a fiber optic bundle. Each lamp is a high intensity unit capable of producing white light without generating harmful amounts of infrared. The lamps can be adjusted over a relatively wide operating range without sacrificing color temperature. Each lamp, when pulsed on or off, exhibits a rise or fall time within the 10 to 100 microsecond range.

In practice, each of the optical elements 18–20 is specially prepared to transmit only light relating to one selected primary color while blocking all other light. The present illumination system is programmed to strobe light into a light entrance face of the fiber bundle in a red, green and blue sequence although any desired firing order may be selected.

Figure 3:
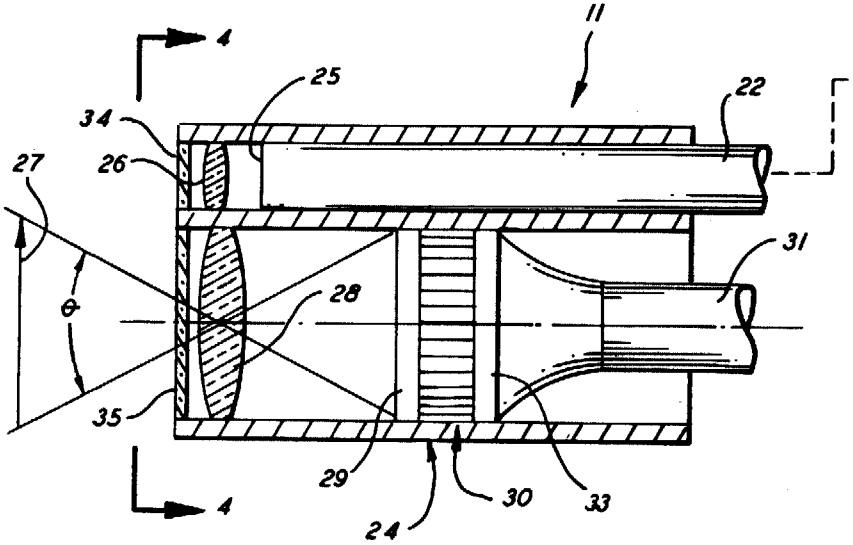
FIG. 3 is a partial view in section showing the illumination system utilized in the present invention.

As seen in FIG. 3, the proximal end of the fiber bundle 22 is trifurcated with each arm being positioned adjacent to one of the optical elements 18–20. The light entrance face of each arm is generally perpendicular to the optical centerline of the adjacent element and lies about within the focal place of the element. Accordingly, a preponderance of the light passing through each element is caused to enter the bundle and is channelled along the flexible bundle into the remote viewing head 11.

The bundle is bifurcated at the distal end thereof to provide for better space utilization in the viewing head and to reduce the shadowing effect normally produced by a single bundle. The three color carrying sections of the bundle are further randomized at the distal end to produce homogeneous mixing of colors in the viewing region and thus provide for uniform illumination during each strobed imaging cycle. The illumination released from the bundle is directed into the object of viewing plane of the system by means of a lens or lens system 26. The lens and the fiber bundle may be either physically or optically adjusted, or both, to produce optimum illumination within the object plane.

Located immediately below the light carrying fiber bundle is an objective or image forming lens 28. The objective is arranged to focus an image of the scene contained in the object plane thereof upon the light receiving surface 29 of a self-scanning solid state imaging device such as charge coupled device (CCD) 30 located in the image plane of the objective. Although a simple lens system is depicted in the drawings, it should be clear to one skilled in the art that a more complex optical system can be herein employed without departing from the teachings of the present invention. Preferably, the objective lens system is provided with a wide angle viewing accommodation wherein the view angle 0 is about 85°.

As disclosed in further detail in the February 1974 issue of Scientific American, a CCD imager contains a number of photosensitive picture elements, generally referred to as "pixels", which are perpendicularly aligned with reference to the optical centerline of the system to form a generally rectangular grid pattern. In operation, light energy falling upon the CCD receiving surface causes electrons contained within each pixel region to accumulate or gather into charge packets. After a timed interval the charge in each packet is applied to an electrode associated with the pixel thereby providing an electrical read-out of the visual image information recorded upon the receiving surface. The data stored in the imager is then clocked out of the element in a line by line sequence similar to that employed in a serial flow shift register. The imager employed in the present invention has a driver-amplifier 33 (FIG. 3) that is operatively associated therewith and which serves both as a means for driving the CCD components and for providing immediate preamplification of the read-out data. Preamplification eliminates unwanted generation of noise or crosstalk in the lines and the driver reduces the number of electrical leads needed in read-out line 31 connecting the imager with external electrical package 32.

Figure 4:
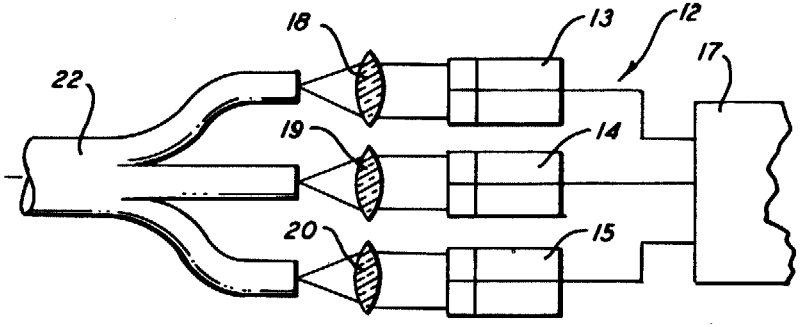
FIG. 4 is a view taken along lines 4—4 in FIG. 3 showing the end view configuration of the viewing head employed in the present invention.
Figure 4:
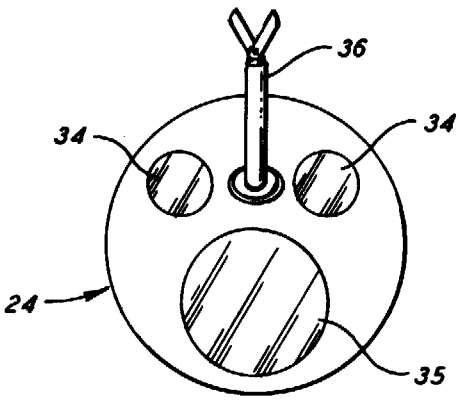

With further reference to FIG. 4, the viewing head includes a pair of illumination windows 34—34 and a single image viewing window 35. As noted, the bifurcated distal end of fiber bundle 22 provides added space within the viewing head whereby components, such as the biopsy device 36 illustrated in FIG. 4, may be conveniently located therein. Means to wash fluids and the like from the windows may also be located in this region along with, or in place of, the biopsy device.

Referring now more specifically to FIG. 1, the electrical section 32 of the system is arranged to accept the visual information signal from the solid state CCD imager and place the information in a format that is compatible with standard video processing equipment. As is typical in most, if not all, standard format television equipment, each picture frame is made up of two interlaced fields of data which combine to provide a faithful rendition of the region viewed. Each field further contains a preselected number of horizontal data lines which are laid down on the viewing screen within a prescribed period of time. Although the number of data lines and the duration of the field periods, may vary, the operation of the video systems remain basically the same.

For explanatory purposes, the apparatus of the present invention will be described in reference to a television format in which each field contains 244 horizontal lines of data which are presented in 1/60 of a second. Accordingly, each frame will contain 488 lines of data and take 1/30 of a second to complete. To accommodate this format, the CCD imager is provided with a $488 \times 358$ pixel grid pattern. The horizontal number of 358 pixels can also be varied depending upon the bandwidth of the receiver and the degree of resolution desired.

In the imaging system shown in FIG. 1, the first field period of 1/60 of a second is utilized to load visual color information supplied by the CCD into three memory units or registers 40, 41 and 42. The three memories are located in a first memory bank 43. In operation, each lamp in the illumination system is triggered once during each field period through means of a strobe drive 17 acting in response to a timing signal from the clock of master timing circuit 45. The master timer may consist of a conventional synchronization generator which is used independently or with logic gates to provide the necessary switching functions that are required in the practice of the invention. Typically, each lamp is flashed on and off at 1/180 of a second interval whereby the region in the object plane of the viewing lens is illuminated in an ordered red, green, blue sequence during each field period.

During the first red imaging interval, the CCD imager accepts red visual image information and converts it to an electrical output data signal that is applied to the preamplification section of the driver amplifier 33 and then passed to video amplifier 38. The interval from illumination to read-out takes 1/180 of a second. At the start of the red imaging cycle, the timing circuit has also conditioned analog switches 46 and 47 to be positioned so that the data signal from the amplifier is clocked into a first memory unit 40. In practice, each unit is preferably an analog CCD chip, however, any suitable shift register for storing this type of data may be used. As will become apparent from the disclosure below, each CCD memory in this particular embodiment is required to store data only during one of the two fields making up a frame and therefore the memory unit utilizes a simplified $244 \times 358$ pixel grid arrangement.

On the following green imaging cycle, the CCD imager is clear of data and is placed in a condition to accept green color information. Here again, the output data signal from the imager is amplified and shifted in a line by line sequence into the first memory 40 in the bank. This action in turn causes the red image data contained in memory 40 to pass serially into memory 41. Similarly on the next blue imaging cycle, blue color information that is generated is shifted into memory 40 whereupon red data passes serially into memory 42 and green data passes into memory 41. This completes the first or odd field period.

At the end of the first field, the master timing circuit causes analog switches 46–48 and 57,57 to be repositioned whereby color information stored in memories 40–42 is simultaneously clocked into the video processor at video-speed. The parallel flow of information is synchronized with the 244 line presentation of the second field by means of the master timer. As this data is being clocked into the video equipment, new data is being fed into a second bank of memories 44 from the CCD imager.

In the video processor 50, the initial three color data is corrected and placed in a form that is acceptable by standard television equipment. As is well known in the art, the processor includes a transmitter matrix for combining the three color signals into composite luminance and chrominance signals that are used in the receiver to control the various picture functions. To obtain instantaneous viewing of the data, the signal is modulated at unit 51 and passed directly to a T.V. receiver 52 for providing a visual presentation thereof. The modulator can be one of many such commercially available radio frequency units that are fully compatible with standard NTSC television matrixes and receivers.

During the second or even field period, the lamps are again strobbed in the noted sequence and the primary color information shifted serially into registers 55, 54, 53 as noted above in a red, green and blue sequence. Upon receipt of the new data, the analog switches are again repositioned through means of timing circuit 45. The stored data is passed in parallel flow into the processor 50. A second field of color information is then processed and is interlaced within the first field to create a high resolution color rendition of the viewing region which can be presented upon the screen of receiver 52, while an odd field is being stored in the memory bank 44.

Figure 2:
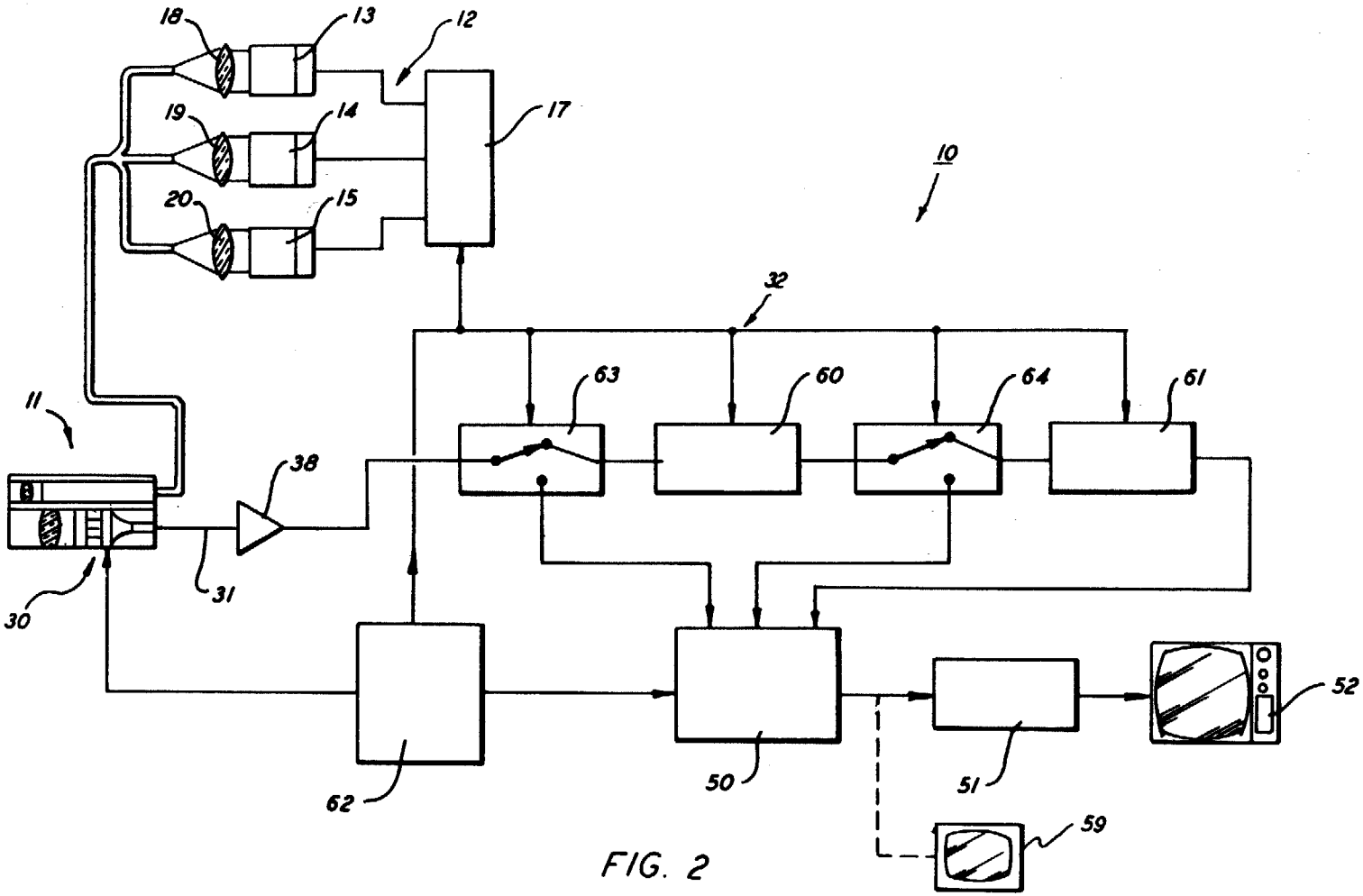
FIG. 2 is a block diagram of a simplified version of the system shown in FIG. 1.

FIG. 2 illustrates a simplified arrangement of the invention wherein the number of memory units needed to create a color picture is reduced. The video processing and viewing equipment 50–52 again is standard format equipment and the illumination system and viewing head remain the same with the like components being referenced with like numerals. Here again, a full screen presentation is furnished. However, because of the reduction in memory units, one field in every frame must be blanked. This causes a reduction in the resolution of the picture but enables a simpler 244×179 pixel format to be employed in regard to the CCD imager. Correspondingly, only two memory units 60 and 61 are required and these memories can be greatly simplified and thus more economical to build.

At the beginning of the first field, analog switches 63, 64 are positioned as shown so that red and green image information clocked out of the CCD imager is shifted serially into memories 61 and 60 respectively. Through means of the master timer 62, each color signal is clocked out of the imager during a 1/120 of a second interval. At the start of the next field, the read-out speed of the CCD imager is changed via the master timer. Switches 63 and 64 are also repositioned so as to feed blue data stored in the imager 30, along with the data stored in the memories 60,61, in parallel flow relationship into the processor 50, through the modulator 51 and finally present the data upon TV receiver 52 as explained above.

As can be seen, in this simplified embodiment of the invention, only one field of each frame is employed to generate a visual display at the TV screen. The second field of the frame, of course, is blanked or grounded out during the period when new data is being stored in the memory units. As a result, the resolution of the picture may be slightly affected due to the lack of interlacing. However, the detail and quality of the picture is more than satisfactory to enable the instrument to be used for its intended purpose.

The circuitry required to produce the color picture is simplified and the cost of the imager and memory units considerably reduced through the use of the 244 line arrangement.

Figure 5:
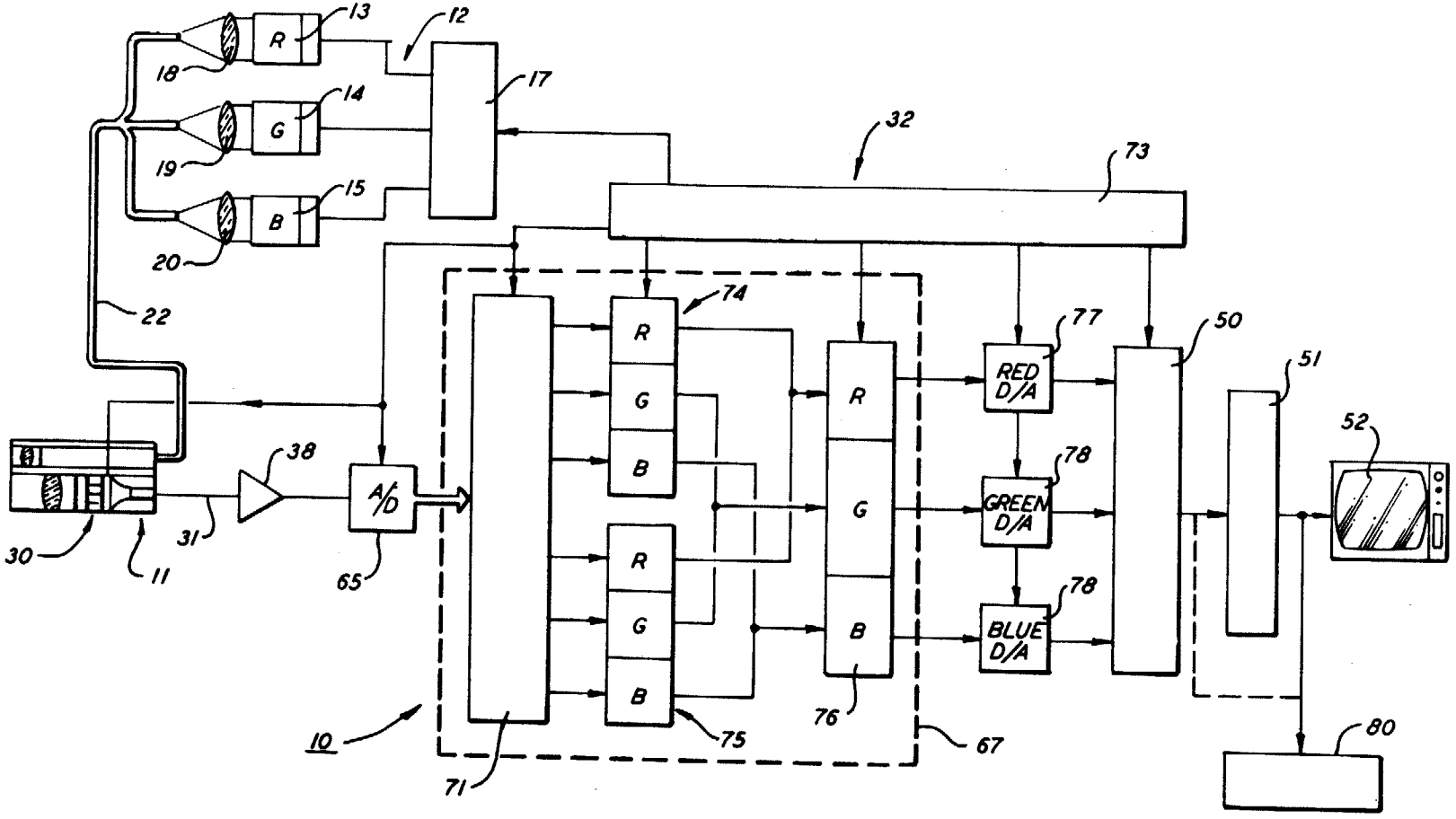
FIG. 5 is a block diagram of an endoscope according to another embodiment of the invention.

Turning now to FIG. 5 there is shown in block diagram form a further embodiment of the invention also utilizing the previously described viewing head and illumination system. Here again, like numerals are used to depict similar or like parts. In this embodiment the output signal of the CCD imager is applied to an analog-to-digital (A–D) converter 65 whose digital output is transmitted to a computer section generally referenced 67. In the A–D converter, color image information clocked out of the CCD imager is placed in six bit digital form. It has been found that a six bit output will contain sufficient information whereby a high resolution picture signal is provided to the video equipment. It should be clear, however, that more or less bits of data can be similarly employed without departing from the teachings of the present invention. The A–D converter output is applied to multiplexer 71 and the data is multiplexed onto one of six output data lines in response to a signal from master timer 73. During the first field, three color data is loaded into a first bank of memory units 74 while during the second field three color data is loaded into a second bank 75, also containing three memory units.

As noted, the CCD imager will preferably have a 488×358 pixel grid arrangement for delivering a full screen interlaced picture at the receiver 52. The lamps 13–15 are thus strobbed at 1/180 of a second intervals to provide one full color field every 1/60 of a second. After the color signals are converted to digital form, they are multiplexed into the two banks of memories 74,75 each of which contains a red, green and blue image retention section.

During the first field, the information stored in bank 74 is passed to output multiplexer 76 and then on to three digital-to-analog converters 77, 78 and 79. In response to a signal from the master timer, the three color signals are simultaneously passed from the D–A converter on to the video processor 50, modulator 51, and video receiver 52 at video speed. During the first field, new color data is being loaded into the red, green and blue memories of the lower bank 75. At the start of the second field the function of the memories is reversed, thereby enabling the system to deliver color data to the video equipment during each field of a frame.

As is well known in the art, an endoscope is typically employed to view the inside of body cavities. It is therefore essential that the viewing head, that is, the portion of the device that is inserted into the body cavity be as small as possible to provide for the safety and the comfort of the subject. As should be apparent from the instant disclosure, because the present device utilizes a single CCD imager in the viewing head, its size can be minimized without sacrificing performance. It should be further noted that the size of the CCD imager can be further reduced by changing the pixel grid arrangement to something less than the 488 line format used in standard TV equipment.

For example, a system using a 244×134 grid pattern may be employed to provide interlacing as disclosed in the inventive embodiment of FIG. 1. In this case, the total area of the picture on the screen is reduced. Although the picture is slightly reduced in size the resolution of the picture, however, is relatively unaffected. Furthermore, in this reduced picture format, the unused portion of the screen may be electronically imaged to present added information relating to the subject being viewed or any other related data that might be desired.

Because the present apparatus is compatible with all standard video equipment, the subject matter being viewed may be video taped for storage and future reference. This can be simply accomplished by applying the output of modulator 51 to any standard video processor 80 as shown in FIG. 5. Similarly, as shown in FIG. 2, raw data taken from the video processor can be sent directly to a standard video-monitor 59 for viewing, thus eliminating the need for video units 51 and 52.

Figure 6:
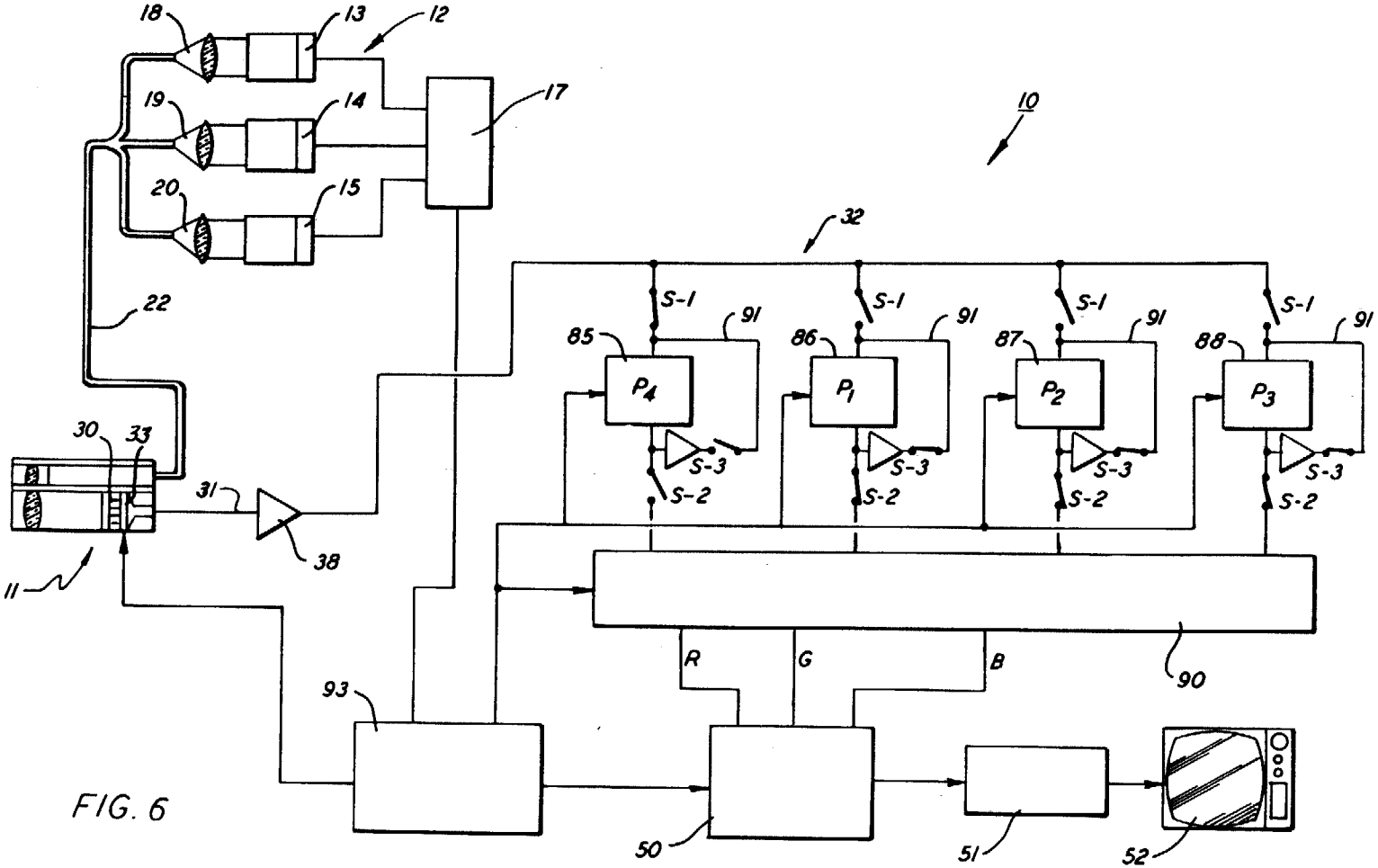
FIG. 6 is a block diagram illustrating a still further embodiment of the invention.

Turning now to FIG. 6, there is shown another embodiment of the invention wherein color data that is stored in a series of memories is continually fed to the video equipment at video speed to provide a full frame, fully interlaced color signal suitable for viewing, tape storage or the like. In this embodiment, however, each primary color signal that is stored in one of the memory units is periodically updated with the up-grading being accomplished at a speed that is considerably slower than video speed. This result is herein achieved using four memory units 85–88. Three of the units feed data to the video equipment while the fourth is being upgraded.

Here again, the remote viewing region is illuminated by light of a primary color through means of the three lamp system as previously described. The light image is used to expose the CCD 30 and an electrical read-out signal indicative thereof is clocked out of the device in a line-by-line sequence. As shown in FIG. 6, the read-out data from the imager can be selectively applied to one of the four memory units. In operation, each of the memories is wired into the system in the same manner. The input signal data is passed from the amplifier 38 into each memory via electrically operated switch S-1. A portion of the output signal is divided out, amplified, and then fed back to the input of the memory via line 91 and electrically operated switch S-3.

In practice, red, green and blue data from the CCD imager is sequentially stored in three of the memories, as for example, memories 86, 87 and 88, by sequentially cycling the associated input switches S-1 in response to a preprogrammed signal from master timer 93. With the color information stored in each unit, the S-2 and S-3 switches associated therewith are simultaneously closed at the beginning of a frame and the stored information is clocked out of the units in parallel flow at video speed.

As the information is being fed out of each unit in a line-by-line sequence, the old data is also being restored in the unit through means of the feedback network. By this means, color image data is continually provided to the multiplexer during one field of each frame while, at the same time, the memories are isolated from the CCD imager.

While data concerning the three primary colors is being forwarded to the multiplexer at video speed, updated data concerning one of the primary colors can be passed from the imager into the fourth memory 85 at a relatively slower speed. During the upgrading period switch S-1 of unit 85 is closed while S-2 and S-3 are opened. Again positioning of the switches is accomplished through means of the timing circuit 93. When memory 85 has been supplied with the desired 244 lines of updated information, the memory containing old data relating to the same primary color is taken off the line by opening associated switches S-2 and S-3 in an ordered timed sequence. Initially S-3 is opened while S-2 is held closed to permit the stored data to be cleared into the multiplexer 90. Once the old data is cleared, switches S-2 and S-3 associated with the upgraded memory are simultaneously closed in timed relationship with the beginning of the next field period whereby the new data is forwarded from the upgraded memory in parallel flow with the remaining stored data into the multiplexer 90. Switch S-1 of the upgraded memory, at this time, is now opened while that associated with the cleared memory is closed.

The memory that has been cleared is now in a condition to receive new or updated data relating to a second primary color whereby the above noted sequence of events is repeated. Each color is thus sequentially updated to continually upgrade the picture information.

The three color data passed into multiplexer 90 is processed, as is well known in the art, and multiplexed out by means of three output data lines. The multiplexed signal is passed on to video processor 50, modulator 51 and viewer 52.

While this invention has been explained with reference to the structure disclosed herein, it is not confined to the details as set forth and this application is intended to cover any modifications or changes as may come within the scope of the following claims.

We claim:

1. In an endoscope of the type having a relatively small viewing head containing a single solid state imaging device for recording light images formed in the viewing region of the head and providing an electrical read-out signal containing the image information, the method of generating a full color standard format video signal including the steps of providing an individual light source for each of the primary colors utilized in the video system at a location that is remote from the viewing head, turning each of the light sources on and off in an ordered sequence, transmitting the light emitted by each source into the viewing region of the head by means of a randomly dispersed bundle of optical fibers whereby image shadowing in the viewing region is minimized, sequentially recording each of the color images on the single solid state imaging device, electrically coupling the read-out signals of the imaging device to a memory, storing the individual color read-out signals in the memory, and periodically forwarding the color signals stored in the memory simultaneously to a processor for [combining the color signals into composite signals that are compatible with a standard format] *placing the signal information in a format compatible with a* color receiver.

2. The method of claim 1 that further includes the step of periodically upgrading the color signal information stored in the memory.

3. The method of claim 1 wherein the light sources emit light of the three primary colors of red, blue and green.

4. The method of claim [3] *1* wherein each primary color signal stored in the memory is updated during each video frame.

5. The method of claim [3] *1* wherein one primary color signal stored in the memory is updated during each video frame.

6. The method of claim 1 that further includes the step of applying the output of the video processor to a standard format television receiver.

7. The method of claim 6 that further includes the step of applying the output of the video processor to a standard format video recorder.

* * * * *

UNITED STATES PATENT AND TRADEMARK OFFICE

CERTIFICATE OF CORRECTION

PATENT NO. : Re. 31,290
DATED : June 28, 1983
INVENTOR(S) : WILLIAM C. MOORE, RICHARD W. NEWMAN & DOMINICK DANNA It is certified that error appears in the above—identified patent and that said Letters Patent is hereby corrected as shown below:

In Claim 1, lines 54 and 55, the words "randomly dispersed" should be in brackets.

Signed and Sealed this

Fourth Day of October 1983

[SEAL]

*Attest:*

GERALD J. MOSSINGHOFF

*Attesting Officer*

*Commissioner of Patents and Trademarks*